US00PP31319P2

(12) United States Plant Patent
Olesen et al.

(10) Patent No.: US PP31,319 P2
(45) Date of Patent: Jan. 7, 2020

(54) CLEMATIS PLANT NAMED 'EVIPO110'

(50) Latin Name: *Clematis viticella*
Varietal Denomination: Evipo110

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSCR A/S, Fredensborg (DK)

( * ) Notice: Subject to any disclaimer, the term of this patent is extended or adjusted under 35 U.S.C. 154(b) by 0 days.

(21) Appl. No.: 15/999,898

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.rhs.org.uk/plants/pdfs/plant-register-supplements/Clematis/6th-Clematis-Supplement.pdf; 2018; 1 page.*

* cited by examiner

*Primary Examiner* — Kent L Bell

(57) ABSTRACT

A new *Clematis* plant with a compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo110'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo110' originated as a single seedling from the stated cross.

The new *Clematis* plant may be distinguished from its female seed parent and male pollen parent by the following characteristics. The female seed parent has white flowers with a diameter of 120 to 130 mm, while the new variety has white flowers with a diameter of 90 to 100 mm. The male seed parent grows to a height of 80 cm in one growing season, while the new variety grows to 180 cm in one growing season.

The objective of the hybridization of this *Clematis* plant was to create a new and distinct variety for nursery culture with unique qualities such as:

1. Uniform and abundant white flowers;
2. Vigorous and compact growth, making the variety suitable for container culture;

3. Improved disease resistance; and
4. Flowering on new growth.

This combination of qualities was lacking in *Clematis* plants that were in commercial cultivation and the qualities have been substantially achieved in the new variety.

'Evipo110' was selected by Mogens N. Olesen and Raymond J. Evison in their *Clematis* development program in the Channel Islands, United Kingdom in 2008. Asexual reproduction of 'Evipo110' by means of vegetative cuttings was first performed by Mogens N. Olesen and Raymond J. Evison in the nursery during the summer of 2008. This initial and subsequent asexual propagations have demonstrated that the characteristics of 'Evipo110' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo110'. Specifically illustrated in the drawing is an open flower, leaves, reproductive flower parts, bare stem, and seed head. Illustrated plants are 2 years of age.

DETAILED DESCRIPTION OF THE VARIETY

The following is a detailed description of 'Evipo110', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo052' described and illustrated in U.S. Plant Pat. No. 28,600 are compared to 'Evipo110' in Chart 1.

CHART 1

| | 'Evipo110' | 'Evipo052' |
|---|---|---|
| Flower diameter | 90-110 mm | 120 mm |
| Tepal upper surface after opening | White Group 155C | White Group 155C with light intonations of Yellow-White Group 158C at the central bar. |
| Plant height | 180 cm | 50 cm |

FLOWER AND FLOWER BUD

Blooming habit: Continuous. The natural flowering period is generally from April to September.

Flower bud:
- *Size*.—Normally 37 mm in length. Bud diameter is 15 mm.
- *Bud form*.—Elliptic.
- *Bud color*.—Yellow-Green Group 147C.
- *Texture*.—Pubescent.

Pedicel:
- *Surface texture*.—Smooth.
- *Length*.—On average 45 mm in length with 1 mm diameter.
- *Color*.—Yellow-Green Group 144A.
- *Strength*.—Moderately strong.

Receptacle:
- *Surface texture*.—Lightly pubescent.
- *Shape*.—Broad funnel.
- *Size*.—1 mm (h)×3 mm (w).
- *Color*.—Yellow-Green Group 144A.

Flower arrangement:
- *Location on vine*.—New growth only.
- *Borne*.—Singly.

Flower bloom:
- *Size*.—On average, flowers are 90-100 mm in diameter and 20 mm in depth.
- *Profile*.—Open flowers are flat to slightly convex.
- *Fragrance*.—None.
- *Lasting quality*.—Flowers normally remain up to 10 days on the plant.

Tepals:
- *Tepal color*.—The upper surface is White Group 155C. The lower surface is White Group 155C with a stripe of Yellow-Green Group 145C.
- *Quantity*.—Normally 6 tepals.
- *Size*.—45 to 50 mm in length by 25 to 30 mm wide.
- *Shape*.—Individual tepal shape is elliptic. The tepal apex is acuminate. The tepal base is typically acute.
- *Apex recurvature*.—Slightly recurved.
- *Tepal overlap*.—Strong.
- *Tepal cross section*.—Slightly reflexed, slightly cupped.
- *Margins*.—Entire. Weak undulations of margin observed.
- *Persistence*.—Tepals drop off cleanly.

Reproductive organs:
- *Pollen*.—None observed.
- *Anthers*.—Size: 5 mm in length. Color: Red-Purple Group 71A. Quantity: On average, 50.
- *Filaments*.—Color: Yellow Group 8C. Length: 10 mm.
- *Pistils*.—Quantity: On average, 60.
- *Stigmas*.—Inferior in location relative to the length of the filaments and the height of the anthers.
- *Styles*.—Color: Yellow-Green Group 145D. Length: 6 mm.

Seed head characteristics:
- *Size*.—45 mm in height. 45 mm in diameter.
- *Quantity*.—About 60 seeds produced per seed head.
- *Style appearance*.—Plumose, semi-erect.

PLANT

Plant form: Climbing.

Plant growth: Vigorous.

Size: Seasons growth attains about 180 cm in height. Average spread is 50 cm.

Stems:
- *Color*.—Juvenile stems are Greyed-Purple Group 183B. Mature stems are Greyed-Orange Group 166A.
- *Internodes*.—On average, 60 to 120 mm between nodes.
- *Length*.—Normally 40 cm from the base of the plant to the flowering portion of the stem.
- *Diameter*.—About 3 mm.
- *Texture*.—Mature stems are slightly ribbed.

Plant foliage:
- *Leaf characteristics*.—Deciduous.
- *Arrangement*.—Varying from ternate to Triternate.
- *Leaf size*.—Compound leaves are 100 to 160 mm (l)×100 to 160 mm (w). Leaflets are 40 to 75 mm (l)×20 to 30 mm (w).
- *Abundance*.—On average 1 to 2 leaves per 10 cm of stem.
- *Leaf color*.—Juvenile upper Yellow-Green Group 144A. Juvenile lower Yellow-Green Group 146C. Mature upper Yellow-Green Group 147A. Mature lower Yellow-Green Group 147B.
- *Stipules*.—Absent.
- *Petioles*.—Size: 40 to 60 mm in length by 1 mm diameter. Texture: Smooth. Color: Brown Group 200A.
- *Petioloule*.—Size: 8 to 35 mm in length by 1 mm diameter. Texture: Smooth. Color: Brown Group 200A.
- *Leaflet shape*.—Lanceolate. The base is rounded and oblique. The apex is acute.
- *Margin*.—Entire, occasionally clefts.
- *Surface*.—The upper side is smooth, the lower side is smooth.
- *Thickness*.—Moderate.
- *Glossiness*.—Not glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo110', substantially as described and illustrated, due to its abundant white flowers with good keepability, attractive long lasting foliage and compact growth, suitability for production from softwood cuttings in pots, durable flowers and foliage which make the variety suitable for distribution in the floral industry.

* * * * *

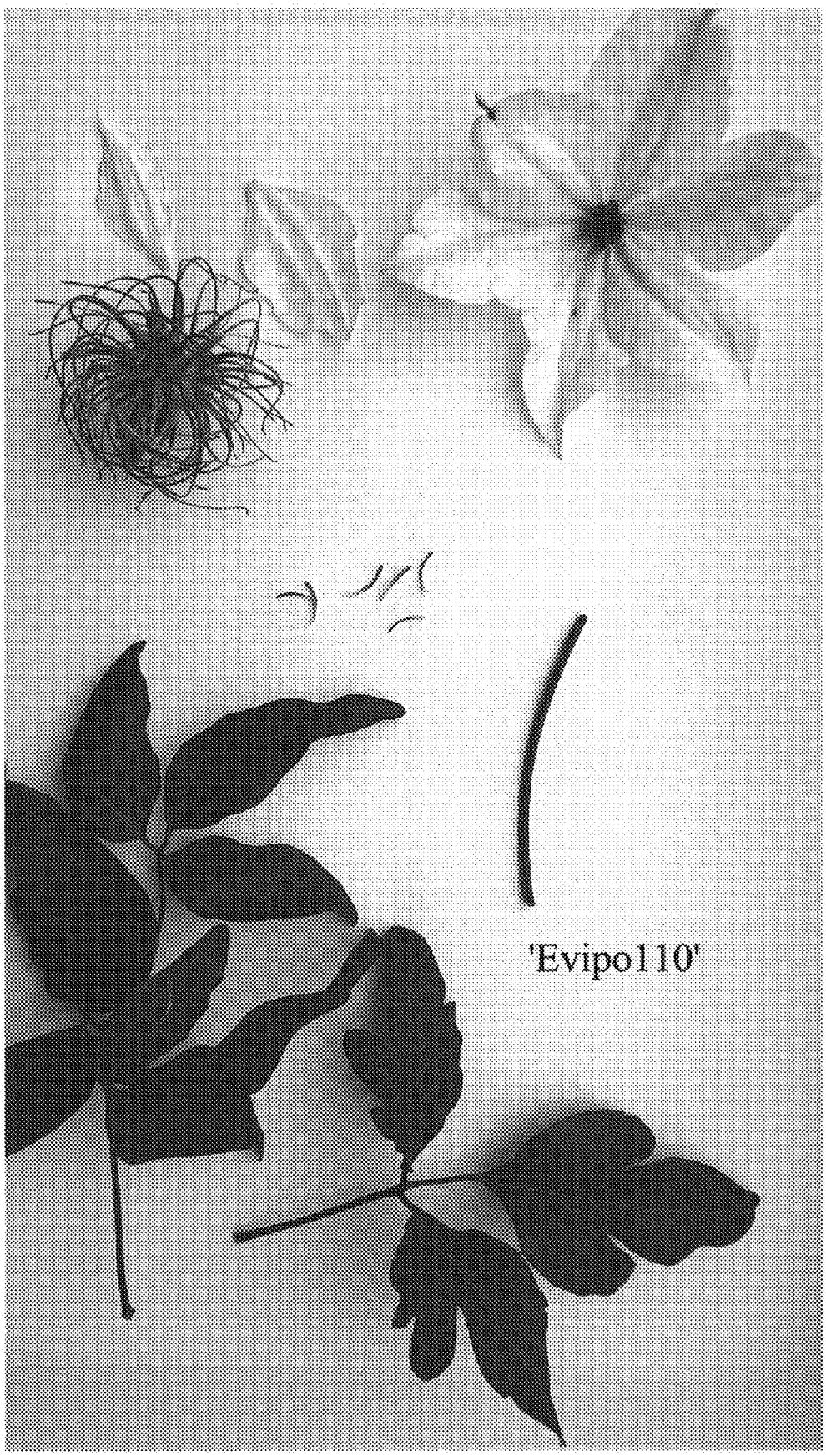
'Evipo110'